US009796626B2

(12) United States Patent
Dosier

(10) Patent No.: US 9,796,626 B2
(45) Date of Patent: *Oct. 24, 2017

(54) PRODUCTION OF MASONRY WITH BACTERIA

(71) Applicant: BioMason, Inc., Research Triangle Park, NC (US)

(72) Inventor: Ginger K. Dosier, Raleigh, NC (US)

(73) Assignee: Biomason, Inc., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/248,996

(22) Filed: Aug. 26, 2016

(65) Prior Publication Data

US 2016/0362334 A1    Dec. 15, 2016

Related U.S. Application Data

(63) Continuation of application No. 14/939,118, filed on Nov. 12, 2015, now Pat. No. 9,428,418, which is a
(Continued)

(51) Int. Cl.
  *C04B 24/12* (2006.01)
  *C04B 24/14* (2006.01)
  (Continued)

(52) U.S. Cl.
  CPC ............ *C04B 24/14* (2013.01); *C04B 14/305* (2013.01); *C04B 24/12* (2013.01); *C04B 28/10* (2013.01);
  (Continued)

(58) Field of Classification Search
  None
  See application file for complete search history.

(56) References Cited

U.S. PATENT DOCUMENTS 4,617,326 A    10/1986  Bjornberg et al.
5,143,155 A     9/1992  Ferris et al.
(Continued)

FOREIGN PATENT DOCUMENTS

CA        2591097       6/2006
CN      101270369 A2    9/2008
(Continued)

OTHER PUBLICATIONS

PCT International Search Report; PCT/US0211/033920; dated Jul. 22, 2011; Dosier, Ginger Krieg.
(Continued)

*Primary Examiner* — Mary Lynn F Theisen
(74) *Attorney, Agent, or Firm* — Remenick PLLC

(57) ABSTRACT

Methods for producing construction material utilizing loose pieces of aggregate (30), enzyme producing bacteria, an amount of urea and an amount of calcium ions. A first solution is prepared which includes urease which is formed by enzyme producing bacteria. A second solution is prepared which includes urea and calcium ions. The first and second solutions are added to the loose aggregate (30). The calcium ions contribute to the formation of calcium carbonate wherein the calcium carbonate fills and bonds between at least some of the gaps between the loose pieces of aggregate forming a solid construction material (92).

19 Claims, 9 Drawing Sheets

Related U.S. Application Data continuation of application No. 14/270,846, filed on May 6, 2014, now Pat. No. 9,199,880, which is a continuation-in-part of application No. 13/834,273, filed on Mar. 15, 2013, now Pat. No. 8,951,786, which is a continuation-in-part of application No. 13/093,335, filed on Apr. 25, 2011, now Pat. No. 8,728,365.

(60) Provisional application No. 61/328,233, filed on Apr. 27, 2010.

(51) Int. Cl.

| | |
|---|---|
| *C04B 28/10* | (2006.01) |
| *C04B 40/00* | (2006.01) |
| *C04B 35/632* | (2006.01) |
| *C12P 1/04* | (2006.01) |
| *C04B 14/30* | (2006.01) |
| *C12N 9/80* | (2006.01) |
| *C04B 103/00* | (2006.01) |
| *C04B 111/00* | (2006.01) |

(52) U.S. Cl.
CPC ........ *C04B 35/632* (2013.01); *C04B 40/0039* (2013.01); *C12N 9/80* (2013.01); *C12P 1/04* (2013.01); *C12Y 305/01005* (2013.01); *C04B 2103/0001* (2013.01); *C04B 2103/0067* (2013.01); *C04B 2111/00017* (2013.01)

(56) References Cited

U.S. PATENT DOCUMENTS

| | | |
|---|---|---|
| 5,891,205 A | 4/1999 | Picardi et al. |
| 6,348,147 B1 | 2/2002 | Long |
| 8,182,604 B2 | 5/2012 | Kucharski et al. |
| 8,420,362 B2 | 4/2013 | Crawford et al. |
| 8,728,365 B2 | 5/2014 | Dosier |
| 8,912,244 B2 | 12/2014 | Vitomir |
| 8,932,400 B2 | 1/2015 | Chen et al. |
| 8,951,786 B1 | 2/2015 | Dosier |
| 9,074,134 B2 | 7/2015 | Bang et al. |
| 9,199,880 B2 | 12/2015 | Dosier |
| 2005/0103234 A1 | 5/2005 | McNulty, Jr. |
| 2008/0245272 A1 | 10/2008 | Kucharski et al. |
| 2010/0086367 A1 | 4/2010 | Darson-Baulleur et al. |
| 2011/0011303 A1 | 1/2011 | Jonkers |
| 2011/0027850 A1 | 2/2011 | Crawford et al. |
| 2012/0199046 A1 | 8/2012 | Jonkers |
| 2013/0112114 A1 | 5/2013 | Jonkers |
| 2016/0090328 A1 | 3/2016 | Jonkers |
| 2016/0264463 A1* | 9/2016 | Dosier .................. C12N 11/14 |
| 2017/0190617 A1* | 7/2017 | Hill ..................... C04B 20/1092 |

FOREIGN PATENT DOCUMENTS

| | | |
|---|---|---|
| EP | 0388304 | 9/1990 |
| EP | 0631998 | 1/1995 |
| EP | 1838642 | 10/2007 |
| EP | 1893546 | 3/2008 |
| EP | 2082999 A1 | 7/2009 |
| EP | 2247551 | 11/2010 |
| EP | 2297062 | 3/2011 |
| EP | 2429970 | 3/2012 |
| EP | 2462232 | 6/2012 |
| JP | 5284646 | 7/2008 |
| WO | WO2006/066326 A1 | 6/2006 |
| WO | WO2007/070706 A2 | 6/2007 |
| WO | WO2008120979 | 10/2008 |
| WO | WO2009.093898 | 7/2009 |
| WO | WO2010/130712 A1 | 11/2010 |
| WO | WO2011/126361 | 10/2011 |
| WO | WO2014/185781 | 11/2014 |
| WO | WO2016/010434 | 1/2016 |

OTHER PUBLICATIONS

Day, Jeremy L. et al, Microbiologically Induced Sealant for Concrete Crack Remediation, http://www.ce.washingtonedu/em2003/proceedings/papers/352.pdf.

Dejong, Jason T. et al, Bio-mediated Soil Improvement; Ecological Engineering, 2009, pp. 197-210, vol. 36, Elsevier.

Dejong, Jason T. et al, Microbially Induced Cementation to Control Sand Response to Undrained Shear, Journal of Geotechnical and Geoenvironmental Engineering, Nov. 2006, pp. 1381-1392, ASCE.

Ferris, F.G. et al, Bacteriogenic Mineral Plugging, Petroleum Society of CIM and CANMET, Paper No. 11, pp. 11-11-12.

Fritzges, Michael B. et al, Biologically Induced Improvement of Loose Sand, Proceedings of the 8th U.S. National Conference on Earthquake Engineering, Apr. 18-22, 2006, Paper No. 1691, San Francisco, US.

Gollapudi, U.K. et al, A New Method for Controlling Leaching Through Permeable Channels, Chemosphere, 1995, pp. 695-705, vol. 30, No. 4, Elsevier Science Ltd., Great Britain.

Kantzas, A. et al, A Novel Method of Sand Consolidation Through Bacteriogenic Mineral Plugging, Petroleum Society of CIM, Jun. 7-10, 1992, pp. 46-1-46-15, Paper No. CIM 92-46.

De Muynck, Willem et al, Microbial Carbonate Precipitation in Construction Materials: A Review, Ecological Engineering, 2010, pp. 118-136, vol. 36, Elsevier.

Nemati, M. et al, Modification of Porous Media Permeability, Using Calcium Carbonate Produced Enzymatically in Situ, Enzyme and Microbial Technology, 2003, pp. 635-642, vol. 33, Elsevier.

Stocks-Fischer, Shannon et al, Microbiological Precipitation of CaCO3, Soil Biology and Biochemistry, 1999, pp. 1563-1571, vol. 31, Elsevier Science Ltd.

Whiffin, Victoria S. et al, Microbial Carbonate Precipitation as a Soil Improvement Technique, Geomicrobiology Journal, 2007, pp. 417-423, vol. 24, Taylor & Francis Group, LLC.

Whiffin, Victoria S., Microbial CaCO3 Precipitation for the Production of Biocement, PhD Thesis, 2004, Murdoch University, Western Australia.

\* cited by examiner

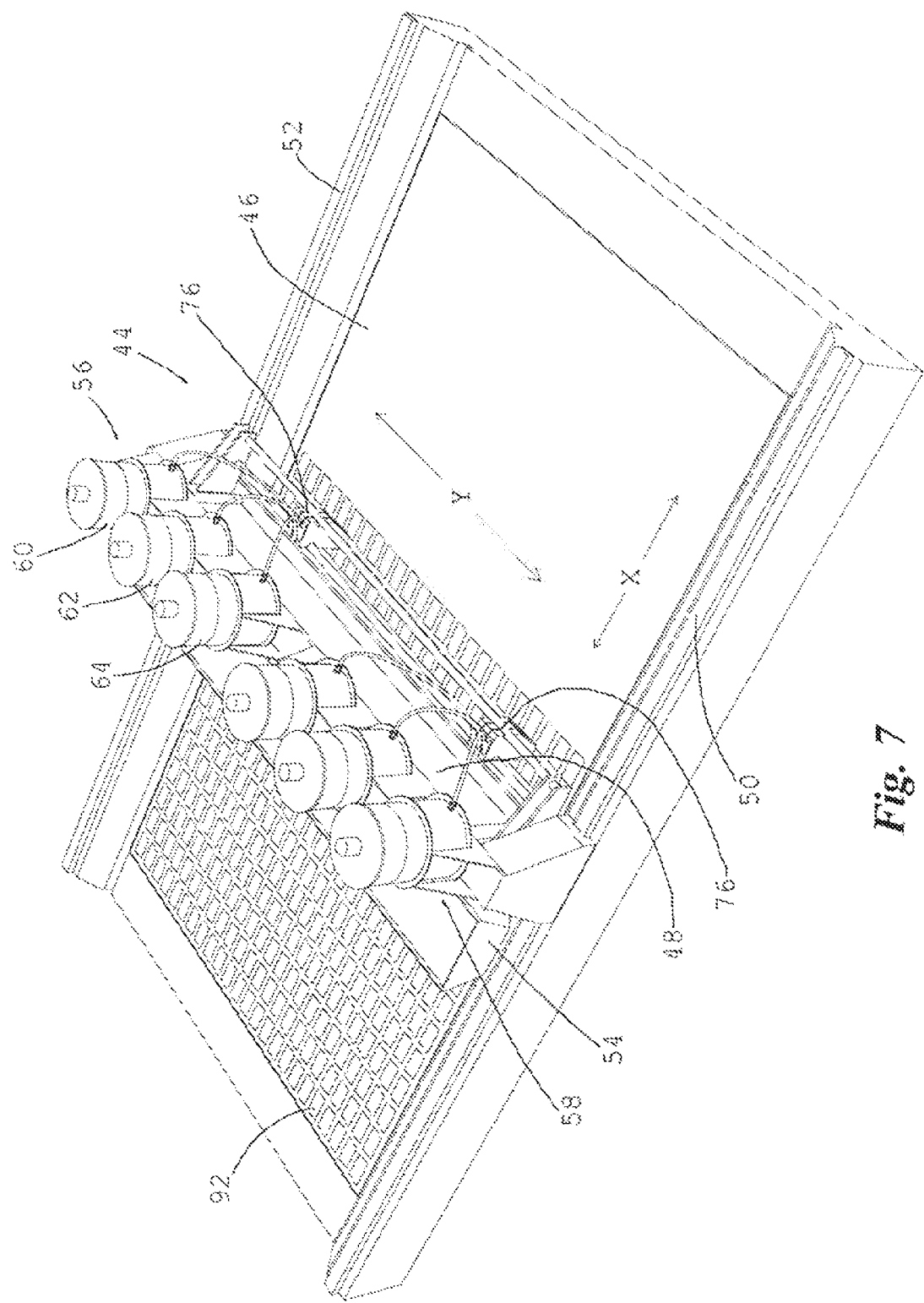

PRODUCTION OF MASONRY WITH BACTERIA

REFERENCE TO RELATED APPLICATIONS

This application is a continuation of U.S. application Ser. No. 14/939,118 entitled "Production and Manufacture with Enzymes and Bacteria" filed Nov. 12, 2015, issued as U.S. Pat. No. 9,428,418 on Aug. 30, 2016, which is a continuation of U.S. application Ser. No. 14/270,846 entitled "Methods for Making Construction Materials Using Enzyme Producing Bacteria" filed May 6, 2014, issued as U.S. Pat. No. 9,199,880 on Dec. 1, 2015, which is a continuation-in-part of U.S. application Ser. No. 13/834,273 entitled "Compositions, Tools and Methods for the Manufacture of Construction Materials with Enzymes" filed Mar. 15, 2013, issued as U.S. Pat. No. 8,951,786 on Feb. 10, 2015, which is a continuation-in-part of U.S. application Ser. No. 13/093,335 entitled "Methods for Making Construction Materials Using Enzyme Producing Bacteria" filed Apr. 25, 2011, issued as U.S. Pat. No. 8,728,365 on May 20, 2014, and claims priority to U.S. Provisional Application No. 61/328,233 filed Apr. 27, 2010, the entirety of each of which is specifically incorporated by reference.

BACKGROUND

1. Field of the Invention

The invention is directed to compositions, tools and methods for the manufacture of construction materials. More particularly, the invention is directed to the manufacture of bricks and masonry blocks as construction materials using isolated enzymes and enzyme-producing cells.

2. Description of the Background

The built environment is primarily constructed using a limited palette of traditional materials: clay, concrete, glass, steel, and wood. Commonly used throughout history, masonry construction continues to make up a large part of the built environment, utilized for both load bearing structures and veneer construction. According to Chaisson, globally, traditional clay brick manufacturing produces over 1.23 trillion units per annum with a heavy dependency on non-renewable natural resources. Clay brick manufactured in coal-powered kilns emits approximately 1.3 pounds of carbon dioxide per unit. According to Burke, in total, brick manufacturing emits over 800 million tons of man-made $CO_2$ each year, and yet represents only one material currently used in building construction.

Fired clay bricks can be manufactured between 3-20 days, depending on the equipment and processes used. This range represents modern automated factories able to process bricks without manual labor, to the clamp method of bricks stacked around a burning fire used in many developing nations.

As an alternative to load bearing fired clay masonry, Concrete Masonry Units [CMU] are widely used as they are more economical, faster to manufacture and can serve as a structural typology for global construction. Comprised of concrete, these units are made with Portland cement, large aggregate and sand filler. According to Hanley of the United States Environmental Protection Agency, global carbon dioxide ($CO_2$) emissions from cement production were approximately 829 million metric tons of $CO_2$ in 2000.

These traditional materials contain a high-embodied energy, with components of concrete and steel mined from non-renewable resources. Approximately, forty-percent of global carbon dioxide is linked to the construction industry, primarily due to material production and disposal. Biologically grown materials can be pollution free and contain a low embodied energy, if produced as part of a local ecosystem.

Natural cement is created through chemical deposition and chemical processes associated with weathering, and can be found in various locations on the earth's crust. The formation of natural sandstones is primarily attributed to the precipitation of calcite cement. As an alternatively to natural deposition, a form of natural cement has been produced with urease producing *Sporosarcina Pasteurii*, a nonpathogenic, common-soil bacterium has the ability to induce the production of calcite through a chemical reaction. The result is a hardened material formed in a process referred to by Stocks-Fischer as microbial induced calcite precipitation [MICP]. Applications include environmental stabilization of contaminated soils, and encapsulation of hazardous and other contaminants in natural soils and acid mine tailings. Ramachandran and Jonkers have proposed the use of microbes to remediate cracks in concrete structures and the repair of cracks in monuments. According to DeJong and Whiffin, civil engineering researchers in the United States, Australia and the Netherlands have proposed the use of MICP for soil stabilization and erosion control.

A need exists for a process to manufacture building materials that does not impose the high energy costs associated with the manufacture of clay bricks and other conventional stone replacement, but utilizes readily available materials and is both economical and environmentally safe.

SUMMARY OF THE INVENTION

The present invention overcomes problems and disadvantages associated with current strategies and designs, and provides new tools, compositions, and methods for the manufacture of building materials.

One embodiment of the invention is directed to methods for producing solid construction materials which preferably is a masonry unit such as brick. A first composition comprises urease which is formed by an enzyme producing cells or otherwise chemically or biochemically synthesized. The enzyme urease where used includes functional variations and mutations thereof. Urease may be synthesized on demand from urease-producing cells, synthesized in bulk from urease-producing cells at a central facility or plant, or chemically prepared at another facility, and by appropriate means which may involve, for example, temperature controls including refrigeration or heat, or liquid or dry conditions, transported to the construction material manufacturing site. Preferably, the enzyme producing bacterium is *Sporosarcina Pasteurii, Sporosarcina Ureae, Proteus Vulgaris, Bacillus Sphaericus, Myxococcus Xanthus, Proteus Mirabilis, Helicobacter Pylori* or a combination thereof, or variant, mutation or genetically modified strain thereof. More preferably, the enzyme producing bacterium is *Sporosarcina pasteurii* or genetically modified strain of *S. pasteurii*.

Preferably, an amount of the enzyme producing cells remains in the first composition after the urease is formed. A formwork is at least partially filled with loose pieces of aggregate wherein gaps are formed between at least some of the pieces. Preferably, the aggregate is sand. An amount of the first composition is added to the loose aggregate. The composition may be added dry and water or another hydrating agent included, or the composition may be added as a liquid. An amount of urea and an amount of calcium ions are added to the loose aggregate. The first composition, the urea and the calcium ions may be added to the loose aggregate simultaneously or at different times or in a different order. The calcium ions contribute to the formation of calcium carbonate. The calcium carbonate fills at least some of the gaps between the loose pieces of aggregate, bonding to the aggregate and thereby forming a solid material. The degree of space-filling can be controlled to provide more or less solid structures. The solid material may be removed from the formwork, or the formwork removed from the material.

Preferably, the formwork is rotated and additional amounts of the first composition, the urea and the calcium ions are added to the loose aggregate prior to removing the solid material from the formwork.

Another embodiment of the invention is directed to methods for producing construction material. A first composition is prepared that includes urease, which is formed by an enzyme producing cells or otherwise added as active enzyme. The first composition may be liquid or dry solid to which liquid is added before use. A solid first composition may comprise freeze dried or otherwise lyophilized enzyme. Lyophilization is a preferred for both storage and transportation as the enzyme can be maintained in lyophilized form for long periods of time (e.g., days to weeks to months) under a wide range of temperatures (e.g., from minus 20° C. to plus 30° C.) without significant loss of activity.

A first layer of loose pieces of aggregate is applied to a substrate wherein gaps are formed between at least some of the pieces within the first layer. A first amount of the first composition is applied to the first layer. An amount of urea and an amount of calcium ions are applied to the first layer. The first composition, which may include water or another hydrating agent, the urea and the calcium ions are applied to the first layer simultaneously or at different times or in a different order. A second layer of loose pieces of aggregate are applied to the first layer so that gaps are formed between at least some of the pieces of the second layer and between at least some of the pieces at the boundary between the first and second layers. A second amount of the first composition is added to the second layer. A second amount of the urea and a second amount of calcium ions are added to the second layer. The second amount of the first composition (which may include water or another hydrating agent) and the second amount of the urea and the second amount of calcium ions are applied to the second layer simultaneously or at different times or in a different order. The calcium ions contribute to the formation of calcium carbonate. The calcium carbonate fills at least some of the gaps between the loose pieces of aggregate, bonding to the aggregate and thereby forming a solid material.

Another embodiment of the invention is directed to methods for producing construction material using a computer numerical controlled (CNC) or numerically controlled (NC) deposition machine having at least first, second and third containers. A first composition is prepared that includes the enzyme urease, which term includes functional variations and mutations thereof. Urease may be synthesized on demand from urease-producing cells, synthesized in bulk from urease-producing cells at a central facility or plant, or chemically prepared at another facility, and by appropriate means which may involve, for example, temperature controls including refrigeration or heat, or liquid or dry conditions, transported to the construction material manufacturing site. A second composition is prepared which includes calcium ions. Preferably, the second composition also includes urea. The first container is at least partially filled with the first composition. The second container is at least partially filled with the second composition. The third container is at least partially filled with an amount of loose pieces of aggregate. A first layer of loose pieces of aggregate from the third container is applied to a substrate. A first amount of the first composition is applied from the first container to the first layer. A first amount of the second composition from the second container is applied to the first layer. A first amount of the composition is applied to the first layer. The first amount of the first composition, the first amount of the second composition, and the first amount of composition are applied to the first layer simultaneously or at different times or in a different order. A second layer of loose pieces of aggregate from the third container is applied to the first layer. A second amount of the first composition from the first container is applied to the second layer. A second amount of the second composition from the second container is applied to the second layer. A second amount of composition is applied to the second layer. The second amount of the first composition, the second amount of the second composition, and the second amount of composition are applied to the second layer simultaneously or at different times or in a different order. The calcium ions contribute to the formation of calcium carbonate. The calcium carbonate fills and bonds between at least some of the gaps between the pieces of aggregate whereby the first and second layers are bonded together and a solid material is formed.

Another embodiment of the invention is directed to methods for producing construction material. A composition is prepared which includes urea, calcium ions and enzyme or enzyme producing cells. The urea and the enzyme react to form urease. The calcium ions in the composition contribute to the formation of calcium carbonate. An amount of loose pieces of aggregate are provided whereby gaps are formed between at least some of the pieces. The calcium carbonate containing composition is added to the aggregate. The calcium carbonate fills at least some of the gaps between the loose pieces of aggregate, bonding to the aggregate and thereby forming a solid material.

As used herein, the term "cells" includes a single type of prokaryotic or eukaryotic cell, a mix of multiple types of cells including animal, bacteria, yeast and algae, and different strains, variations, mutations and genetically engineered forms of any of the preceding. Also as used herein, the term "formwork" includes frames, forms, molds, and other apparatus which may be used to hold loose pieces of aggregate together before the pieces are bonded in accordance with the teachings of this invention. Material remains in the mold and cures for seconds to minutes to hours or days, depending upon the amount and type of material, the temperature, pressure, humidity, environmental conditions, and the amount of urease, the amount of calcium and the amount of urea. Preferably curing times are on the order of seconds, minutes, hours or days for larger building materials. Alternatively, partially cured material may be transferred to an atmospheric chamber for further curing under defined conditions. Also as used herein, the term "solid construction material" includes construction material which is porous and non-porous.

Embodiments of invention utilizes MICP and methods are defined to fabricate full-scale construction materials, including load bearing masonry which may be pre-cast. The benefits of a construction material that can be "grown" go beyond issues of economy and sustainability. As this is a material made by aggregation, additional materials can be added to the composite for additional performance traits, such as fibers for additional strength, Titanium Dioxide [$TiO_2$] for pollution absorption, glass beads for the transmission of light, and/or air-entrained aggregates for insulation. MICP materials mimic the properties of natural sandstone and are composed of similar crystalline formations.

Another embodiment of the invention is directed to methods for manufacture of a solid component comprising: providing a formwork and, in any order, adding an aggregate and a composition containing urease or urease-producing cells to the formwork, together forming a combination of ingredients; mixing the combination of ingredients either before or after addition to the formwork; curing the combination of ingredients thereby forming a solid. Preferably the composition is added to the formwork by placing, pressing, forming or extruding. Preferably the solid component is a concrete masonry unit, a cinder block, a brick, a foundation block, a breeze block, a hollow block, a solid block, a besser block, a clinker block, a high or low density block, an aerated block, a tile or pre-cast veneer, wherein the formwork typically determines the shape and size of the solid component. Preferably the composition contains urease and the amount of the urease added is from about 0.05-20.0 mg/ml of fluid or the composition contains urease-producing cells and the amount of the urease-producing cells added is from about $10^5$/ml to $10^{10}$/ml of fluid, and more preferably from about $10^6$/ml to $10^8$/ml. Preferably the composition further contains calcium and preferably, the amount of calcium added is from about 0.1-500 mg/ml of fluid. Preferably the composition further contains urea and preferably, the amount of urea added is from about 1-200 g/L of fluid, more preferably from about 5-100 g/L of fluid. Preferably the amount of the aggregate added is from about 1 kg to about 100 kg, but is preferably a size that can be most easily utilized in construction. Preferably, the aggregate, the urease and the calcium ions are mixed prior to being added to the formwork, or the aggregate, the urease and calcium ions are added simultaneously or sequentially. Preferably, curing comprises atmospheric conditions at ambient temperatures, but can comprise curing with added heat and/or humidity (e.g., steam, vapor or spraying). The method also comprises rotating the formwork; adding an additional amount of the composition to the formwork; simultaneously or at different times or in a different order. Preferred construction material is shaped as a brick or a block. Preferably, the first solution comprises enzyme producing cells and the enzyme producing cells are bacteria selected from the group consisting of *Sporosarcina pasteurii, Sporosarcina ureae, Proteus vulgaris, Bacillus sphaericus, Myxococcus xanthus, Proteus mirabilis, Helicobacter pylori* and variants, mutations and combinations thereof. Also, preferably, calcium chloride, calcium acetate, calcium phosphate, calcium carbonate, calcium lactate, or a calcium salt, is a source of the calcium ions.

Another embodiment of the invention is directed to solid components manufactured by the methods of the invention, and the components are utilized in a multicomponent structure. Preferably the multi-component structure is a wall, a building, a road, or a combination thereof. Also preferably the solid component contains pores of at least five microns. Components may be of any size and shape, and are preferably rectangular, square, rounded, oval or an irregular shape. Another embodiment of the invention is directed to kits comprising: a composition containing urease-producing cells in a transport media or urease in an enzymatically acceptable carrier; and a frame that supports the addition of an aggregate and the composition for the formation of a solid unit. Preferably, the urease-producing cells are eukaryotic or prokaryotic cells and the transport media is minimal growth media. Also preferably, the composition further contains one or more of urea, calcium and water and, preferably is lyophilized. Preferred packages or kits further contain instructional materials for manufacture of construction materials and the preferred construction materials are bricks.

Other embodiments and advantages of the invention are set forth in part in the description, which follows, and in part, may be obvious from this description, or may be learned from the practice of the invention.

DESCRIPTION OF THE DRAWINGS

FIG. 7 is perspective view of a computer numerical controlled deposition machine which may be used to produce construction material in accordance with the teachings of an embodiment of the invention;

DESCRIPTION OF THE INVENTION

Figure 1:
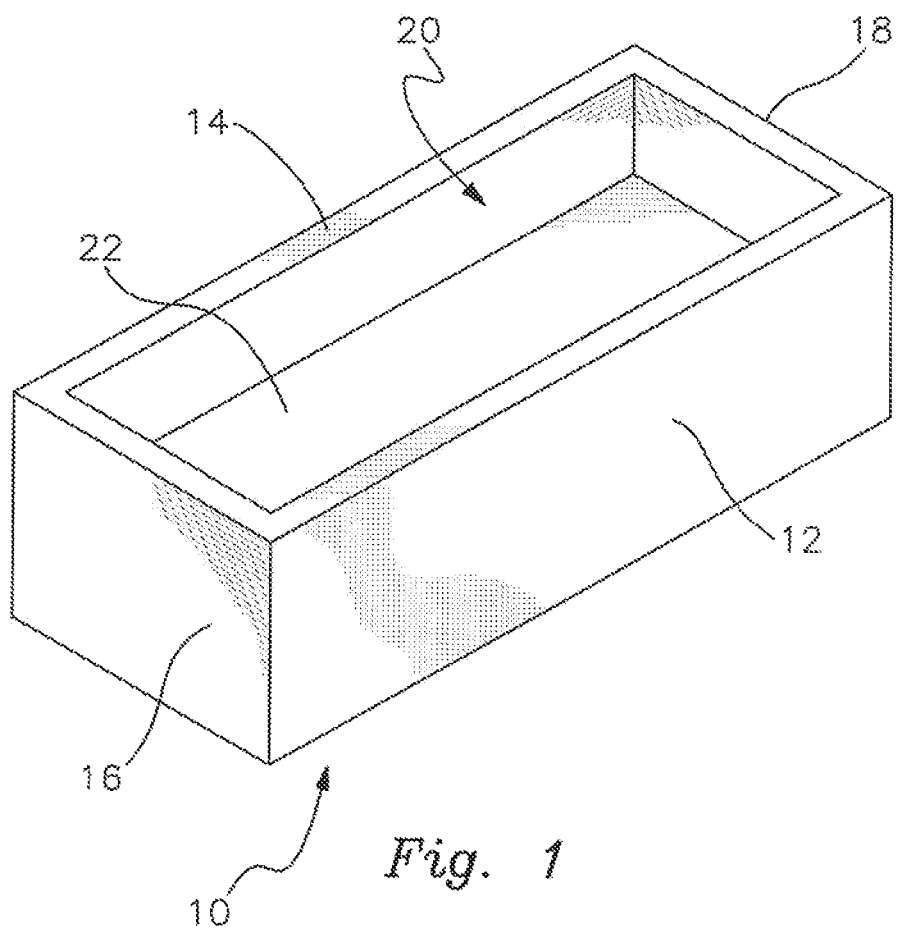
FIG. 1 is a perspective view of a formwork which may be used in connection with the manufacture of construction material embodying the invention.

*Sporosarcina pasteurii*, a nonpathogenic common soil bacteria, has the ability to induce a cement material that can fuse loose aggregate, such as grains of sand. Other aggregates such as glass beads, recycled glass foam, fly ash composite, soil, small stones, basalt, fibers, and mixtures of the above may also be used. Ideally, local aggregate would be used from, distilled directly from the location where the units are to be manufactured. If the pieces of aggregate, such as sand, are fused in a formwork or deposited in layers and treated in accordance with the teachings of this invention, construction materials, which are preferably masonry units such as brick, blocks, or any size and shape of a structural component may be manufactured and, as desired, easily mass produced. The teachings of this invention could further be used to produce pre-cast elements such as panels, columns, tiles, counter-tops, and/or any other construction unit commonly produced using sand, gravel, asphalt, clay, brick, concrete, and/or stone, any of which may be recycled material. A hardened material is formed in a process known as microbial induced calcite precipitation [MICP]. The cells or enzyme may be mixed in a composition of urea and calcium chloride. Certain cells produce urease using urea as a source of energy. The enzyme catalyzes the production of ammonia and carbon dioxide, increasing the pH level of the composition. The rise in pH forms a mineral "precipitate," combining calcium with carbon dioxide. The cells or other particles can then act as nucleation sites, attracting mineral ions from the calcium to the cell wall, forming calcite crystals. The mineral growth fills gaps between the sand grains, biocementing or bonding them together. Preferably, the gaps are at least 5 microns in width, but can be larger or smaller as desired. The resulting material exhibits a composition and physical properties similar to naturally formed sandstone, but whose hardness can be predetermined based at least on the structure of the initial components and the pore size desired.

Other enzyme producing bacteria that are capable of biocementation include *Sporosarcina ureae, Proteus vulgaris, Bacillus sphaericus, Myxococcus xanthus, Proteus mirabilis* and *Helicobacter pylori*, although proper concerns should be given to pathogenic strains. Combinations of any of these strains as well as functional variants, mutations and genetically modified stains may be used as well. Compositions of the invention may contain nutrient media to maintain and/or allow the cells to flourish and proliferate. The various types of nutrient media for cells, and in particular, bacterial cells of the invention are known and commercially available and include at least minimal media (or transport media) typically used for transport to maintain viability without propagation, and yeast extract, molasses, and corn steep liquor, typically used for growth and propagation. As compositions of the invention may contain specific identifiable cells, it is also possible to determine the origin of a particular brick or structure by performing a simple nucleic acid analysis. Provided the genome of the urease-producing cells is not otherwise native to the area, or is unique, the structure can be identified as masonry of the invention and all locations tracked. Alternatively, unique nucleic acid sequences or other identifiable tags such as unique chemical codes can be included into the compositions of the invention.

Compositions of the invention alternatively may include isolated urease enzyme. Commercial sources of urease include, for example, jack beans. Enzyme can be maintained as a liquid, but are preferably lyophilized for ease of storage and transport, and re-hydrated before use with water, buffered water or another hydrating agent that preserves enzyme activity. Preferable, pure enzyme is encapsulated in carbohydrate, lipid or other polymer microshells or spheres. Encapsulation techniques include, for example, encapsulation in nanoorganized microshells, and encapsulation in xanthan-alginate spheres. Preferred enzyme concentrations are from 0.5-5 mg/ml in 0.1 M phosphate buffer, pH 7.6. Preferably enzyme concentrations are from about 0.1 to 100 mg/ml, more preferably about 0.5 to 3.0 mg/ml, more preferably from about 0.5 to 2.0 mg/ml, and more preferably about 1.0 mg/ml. Enzyme can be further diluted prior to use to obtain a rate of 0.02-0.04 AA/minute. Enzyme activity can be measured by the reaction:

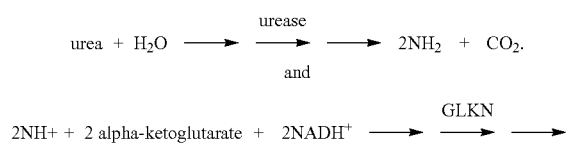

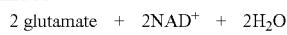

which couples ammonia production to a glutamate dehydrogenase reaction. Accordingly, one unit of enzyme results in the oxidation of one micromole of NADH per minute at 25° C. and pH 7.6.

This method for manufacturing construction materials through induced cementation exhibits low embodied energy, and can occur at ambient pressure, and in a range of temperatures from at least minus 20° C. to above 80° C. Preferably, the temperature range is below 30° C., below 40° C., below 50° C., below 60° C., or below 70° C. The ambient temperature and conditions as well as the content of available aggregate can determine whether pure enzyme, lyophilized enzyme, or live cells are utilized as the starting components. Generally, live cells are used in warmer temperatures where mild weather conditions exist, whereas pure enzymes can be advantageous at more extreme conditions of cold or heat. Traditional brick and concrete construction is heavily reliant on burning natural resources such as coal and wood. This reliance results in the consumption of massive amounts of energy resources and equally massive carbon dioxide emissions, thus a great dependency on limited energy sources. The introduction of a bioengineered building unit using sand aggregate and naturally induced cementation offers a natural alternative that may be locally produced and environmentally friendly. As little to no heating is necessary, the energy savings in both expenses and efficiency is enormous.

Another advantage of the invention is that the process can be utilized in both small and large scale, and also easily automated. The bulk content of the brick manufacturing process of the invention can be most any material that is locally available including rocks, sand, gravel and most any type of stone. Processing of the stone, such as crushing or breaking into pieces, also can be performed locally. Thus, transport costs and expenses are minimized. The composition of the invention (which may be provided lyophilized and hydrated on site), the frame for the bricks (if otherwise unavailable), and instructions as appropriate are all that need to be provided. If shipping is required, this represents a tiny fraction of the delivery costs, especially as compared to the present expenses associated with the delivery of conventional cement. Accordingly, another embodiment of the invention includes kits comprising a composition of the invention and, if necessary, the desired frame structure. The composition of the invention can comprise, urease or, preferably, urease-producing cells, urea or hydrolyzed urea (e.g. forms of ammonia), nutrient broth if using cells, and a source of calcium. Preferably the ingredients are packaged together but one or more may be separated and packaged individually. Compositions of the invention may be provided in aqueous form or lyophilized or provided frozen or otherwise in an inactive state. Enzyme inhibitors may be added that are removed or sufficiently diluted before use. Compositions containing cells may be supplied live, but otherwise separate from the nutrients necessary to allow the cells cultures to proliferate and produce urease.

Another advantage of the invention is that many of the initial ingredients are readily available. For example, sources of calcium are often locally available from, for example, local geology such as limestone, milk and milk products and by-products, egg shells, lakes and rivers, sea water, and plant materials to name a few. Preferably, calcium is used as a source when in the form of a salt such as, preferably, calcium chloride, calcium carbonate, calcium lactate, calcium acetate, calcium phosphate and calcium sulfate. Many of these forms are readily available in different parts of the world. Also readily available in most parts of the world is urea. As a chemical salt, it can be easily obtained from urine which is available from livestock and agricultural sources, as well as municipal sources. Thus, compositions of the invention may include a calcium source and/or urea, and/or the calcium source and/or urea may be obtained separately.

Another advantage of this invention is to produce a "grown" construction material, such as a brick, utilizing primarily minerals, MICP and loose aggregate, such as sand. Not only can bricks and other construction materials be created, but the bricks themselves can be cemented into the desired places using the composition of the invention to "cement" the bricks to one another and/or to other materials thereby forming the buildings, support structure or member, walls, roads, and other structures.

As collaboration between architecture and microbiology, this invention enables one to use MICP, in conjunction with local sand aggregate, for the creation of a "biologically grown" building material, to be used by the construction industry. "Brick" manufacturing can be achieved utilizing traditional casting methods, or articulated by digital tooling to fabricate layered units with a programmed material composition. The use of computer numerical controlled (CNC) manufacturing technologies is economically driven as it generates little waste, accommodates a variety of potential materials, provides a high degree of accuracy, and allows for the mass customization of form, consistency, and material distribution. The brick can be digitally modeled to specifically and precisely locate mineral templates for growth, and different sizes of aggregate for intended performance. Programmed, layered growth allows for the ability to vary dimensions within the brick, just as bone varies in orientation and density throughout its length, becoming thicker and thinner in places. Bricks of the invention can be the same and structure as clay bricks, cinder blocks or any conventional construction materials. Preferably the bricks or blocks are partially or uniformly porous containing a network of holes or gaps of at least 5 microns in diameter, at least 10 microns in diameter, at least 20 microns in diameter or at least 50 microns in diameter. Also preferably the bricks or blocks contain openings to reduce overall weight, yet maintain support strength. It has been surprisingly discovered that traditional bricks of the invention provide greater compression strength than clay bricks.

The biological bricks of the invention do not require the traditional use of Portland cement mortar, rather they use the same process during biomanufacture for connection. During the construction process, the completed bricks may be "dunked" into a slurry of cells, growth media, and/or aggregate prior to placing them together. The bricks fuse over a period of time as the cells induced precipitation bonds the aggregate grains together, preferably with calcite.

This invention enables the reduction of atmospheric carbon dioxide by offering an alternative to the high-embodied energy traditionally manufactured construction materials. Employing cells to naturally induce mineral precipitation, combined with local aggregate and rapid manufacturing methods, this invention enables the production of a local, ecological, and economic building material for use throughout the global construction industry.

Another embodiment of the invention is directed to compositions of the invention that are useful in 3D printing. Compositions can be combined in a controlled fashion to be continuously layered forming a structure as determined by the 3D replication software. 3D printers are commercially available and can be modified by one skilled in the art to utilize compositions of the invention.

In accordance with one embodiment of this invention, a formwork, such as formwork 10 shown in FIG. 1, is used to contain the aggregate, such as sand, while the aggregate is being treated with composition or solutions containing urease, calcium ions, urea, nutrient and preferably, an enzyme producing cells. Preferably, the urease is formed by exposing an amount of urea to the enzyme producing bacteria, such as *Sporosarcina pasteurii*. Formwork 10 includes first, second, third and fourth vertical walls 12, 14, 16 and 18, which are connected together forming cavity 20 therebetween. Cavity 20 is adapted to receive the loose pieces of aggregate such as sand. Formwork 10 may also have a floor 22. Alternatively, the bottom of the formwork may be left open if supported by a porous surface such as soil, or aggregate and composition may be mixed and pressed into molds or extruded.

Preferably, vertical walls 12, 14, 16 and 18 or at least the inside surfaces thereof, are made of a non-reactive, non-porous material such as cast or extruded acrylic resin. This enables one to easily remove the construction material or the brick from the formwork 10 after it has solidified. In addition, the vertical walls and floor of formwork 10 may have textures to form textures in the resulting brick.

Another advantage of the invention is that the bricks are formed without a need to subject the curing mixture to intense pressure as is necessary for clay bricks. Manufacturing processes form the bricks into structures according to the shape of the formwork, which can vary greatly and be used to create more sophisticated forms as the need for the form to withstand intense pressure is no longer required.

Figure 2:
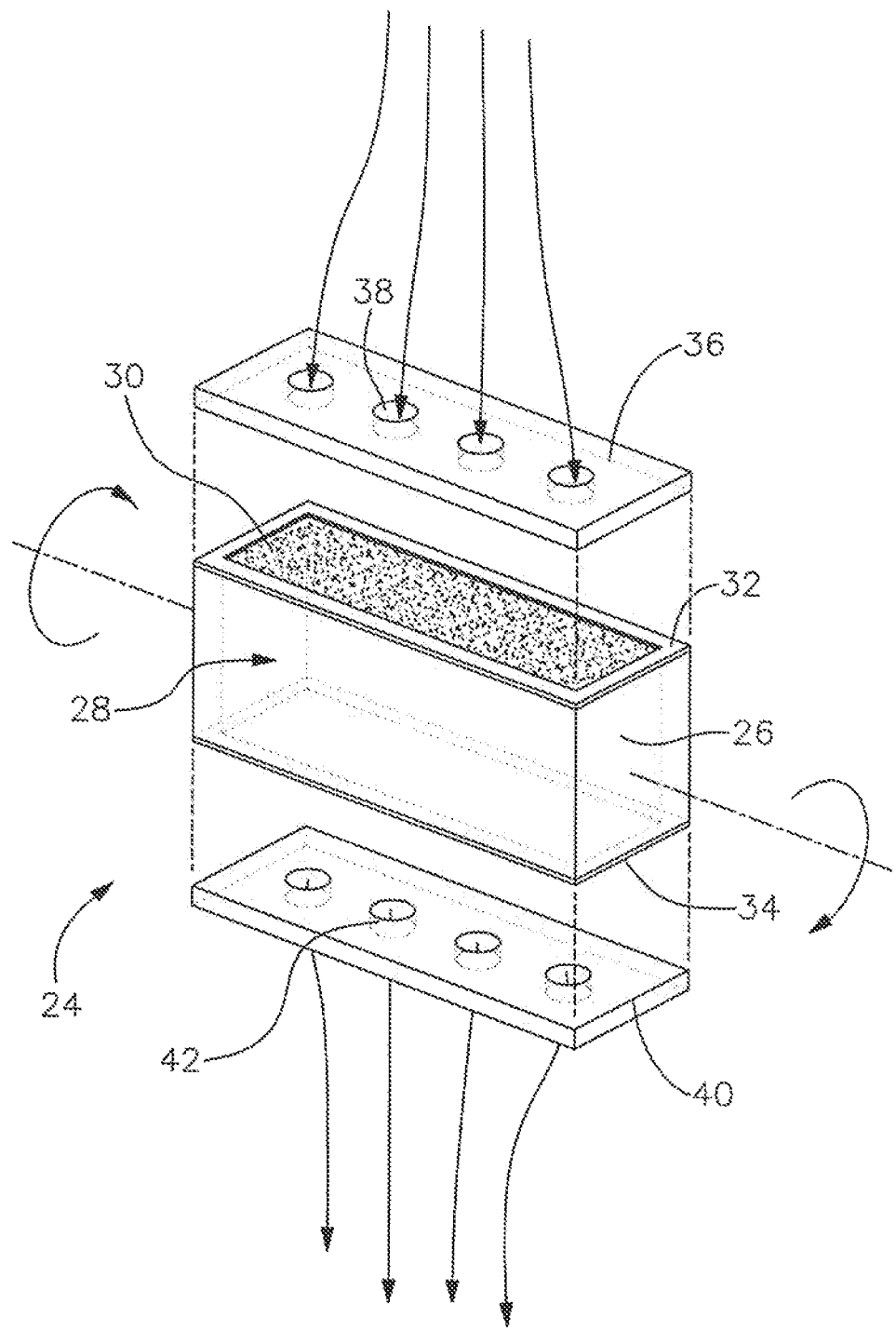
FIG. 2 is an exploded pictorial view showing another embodiment of the formwork of FIG. 1.
Figure 11:
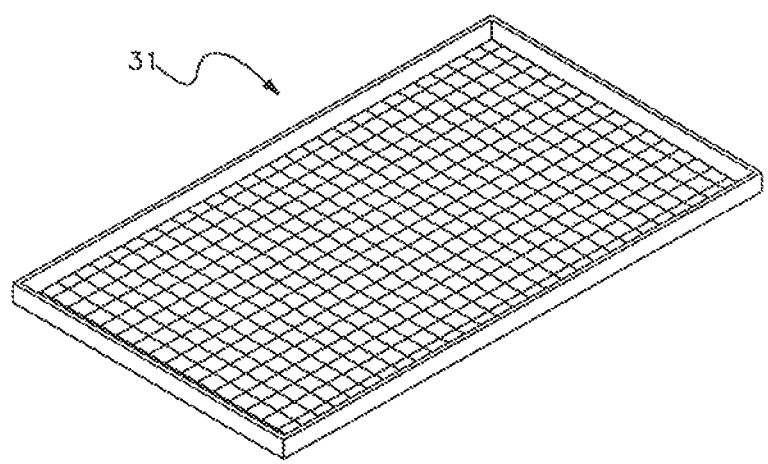
FIG. 11 is a perspective view of a screen which may be used to filter pieces of aggregate material in accordance with the teachings of this invention.

FIG. 2 shows, an alternative of the formwork of FIG. 1 which is able to be rotated so that the solutions more fully penetrate into the sand for more uniform cementation. Formwork 24 includes four vertical side walls 26 made of non-porous non-reactive material as described in reference to FIG. 1. Cavity 28, formed by the vertical side walls 26, is filled with an aggregate material 30, such as sand. Preferably, the pieces of aggregate are filtered by a known aggregate filter, such as screen 31 shown in FIG. 11, so that specific aggregates with specific consistencies and make-up may be placed in the formwork. Alternatively, thin layers of aggregate may be added to cavity 28 over time with each layer being separately treated with the solutions. The top and bottom of side walls 26 include moisture seals 32 and 34. A top removable panel 36 interfaces with moisture seal 32. The top removable panel is also made of non-porous non-reactive material. The top removable panel 36 includes a plurality of influent openings 38. A bottom removable panel 40 interfaces with moisture seal 34. The bottom removable panel is also made of non-porous non-reactive material. The bottom removable panel 40 includes a plurality of effluent openings 42. As will be described below, when formwork 24 is rotated 180°, the effluent openings 42 become influent openings and vice versa. Influent openings 38 and effluent openings 42 may be connected to hoses to permit application and drainage of solutions containing urease, calcium ions, urea and preferably the cells. As cementation primarily occurs near the top portion of the aggregate material, that cementation can block the passage of additional amounts of solution further into the interior of the aggregate material. The embodiment of FIG. 2 permits the formwork 24 to be rotated, which in this embodiment is 180°, so that the openings 42 of bottom panel 40 become influent openings and the openings 38 of top panel 36 become effluent openings. This rotational feature enables better penetration of the solutions into the aggregate. The use of a plurality of influent openings provides for a more equal distribution of the solutions. In addition, the inner faces of the vertical walls 26 and the panels 36 and 42 may be textured, enabling better physical connections during assembly and/or for giving an aesthetic appeal to the bricks. In addition, a positive bump out on the inside surface of one or more of the vertical walls 26 and/or the inside surface of one or more of the panels 36 and/or 40, may be provided so that the resulting brick will have a hollowed out region or regions.

Figure 10:
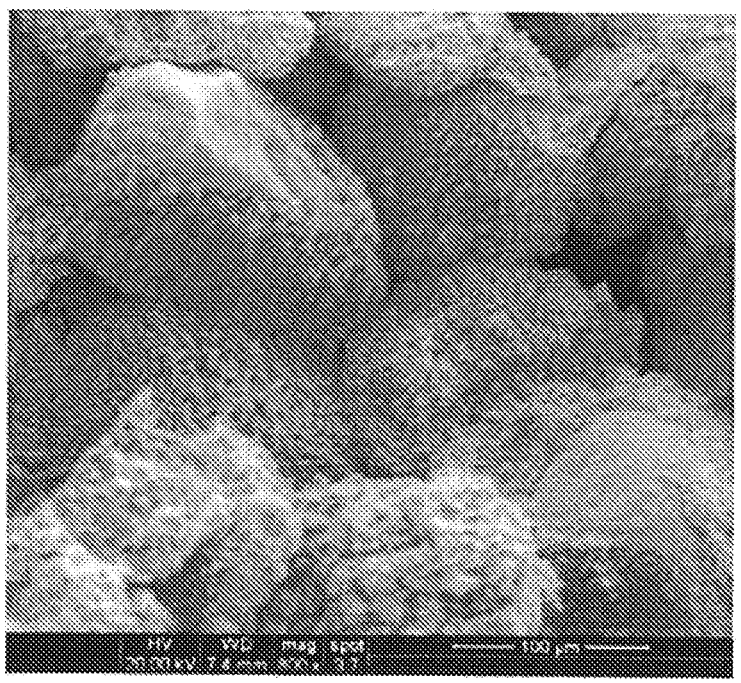
FIG. 10 is a photomicrograph showing bonding of certain gaps between loose pieces of aggregate with calcium carbonate.

The embodiment of FIG. 2 enables the solutions to be added to the aggregate purely by gravitational means without the requirement to mechanically force the solutions into the aggregate. The rotation of formwork 24 after a number of treatments ensures homogeneity in cementation and strength. Calcium carbonate crystals will grow along these aggregate surfaces where solutions are found, due to the surface tension along the pore throat formed between the aggregates. Rotation helps to ensure the equal growth of calcium carbonate around aggregate particles. The bonding of the calcium carbonate to adjacent aggregate particles is illustrated in FIG. 10. To achieve an even higher cementation depth, the formwork can be rotated along multiple axes for access to all sides. For example, if a six-sided rectangular brick is desired, there are three possible axes for rotation. The embodiment of FIG. 2 shows a single axis of rotation. In addition, this rotational method can be used in conjunction with the lamination or layered method which will be described below.

Figure 3:
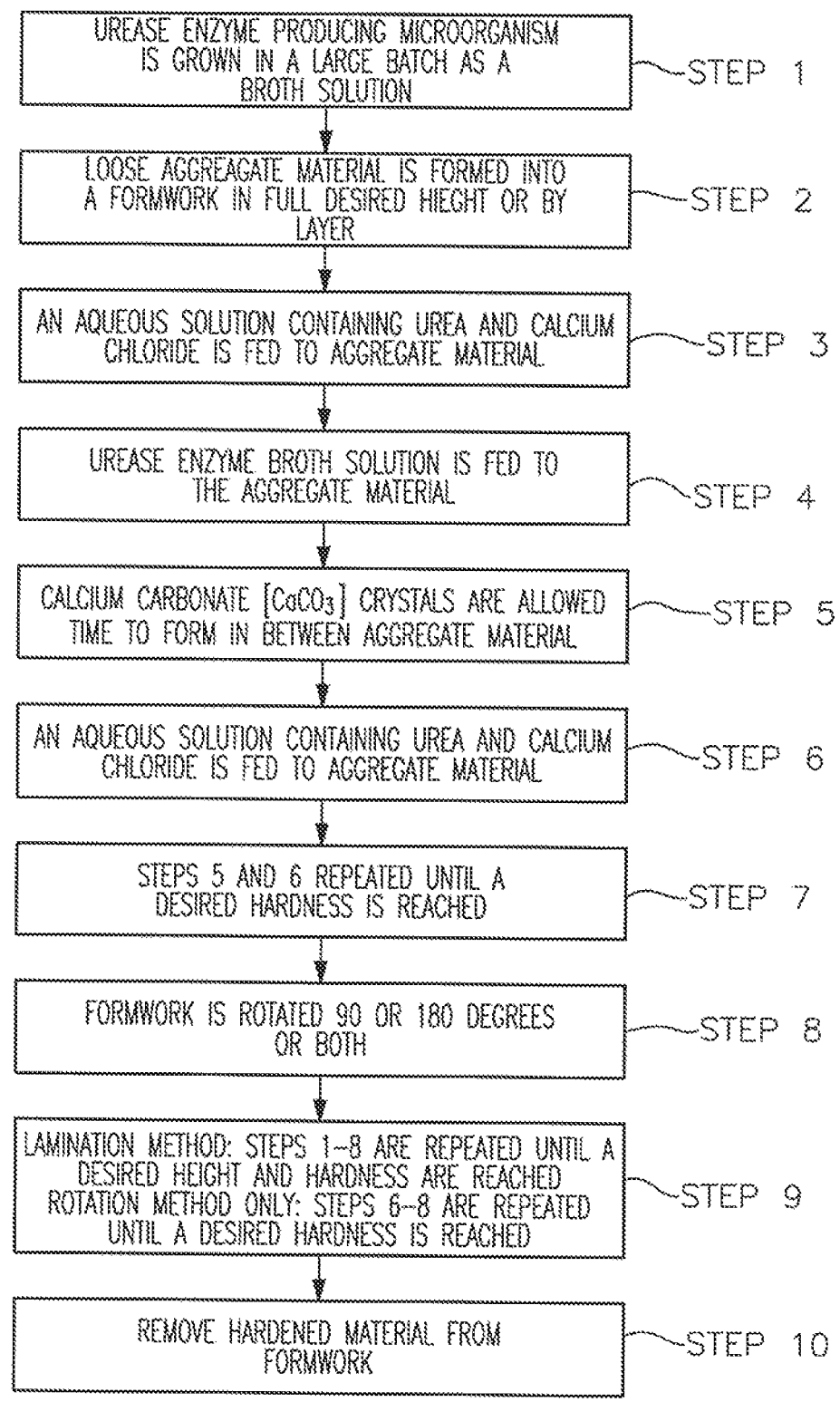
FIG. 3 is a flow chart showing steps for the production of construction material in accordance with one embodiment of the invention.

Steps 1 through 8 of FIG. 3 illustrate the rotational method of manufacturing the brick. Step 9 of FIG. 3, when combined with Steps 1 through 8, illustrates the combination of the rotational method and lamination method. In the lamination method, discrete layers of aggregate are separately deposited and individually treated with the solutions.

Referring now more particularly to FIG. 3, in Step 1, a urease producing bacteria is grown as a broth solution. The preferred urease producing bacteria are *Sporosarcina pasteurii, Sporosarcina ureae, Proteus vulgaris, Bacillus sphaericus, Myxococcus xanthus, Proteus mirabilis*, and *Helicobacter pylori*. The most preferred urease producing bacteria is *Sporosarcina pasteurii* in part due to it being non-pathogenic. In addition, growth material such as yeast extract or peptone from soy is added to the broth to help enable the bacteria to multiply. In Step 2, loose pieces of aggregate material, such as sand, is inserted into the cavity 30 of formwork 24 to the desired height. In the lamination method, only a relatively thin layer of loose aggregate is added. Gaps are formed between at least some of the pieces of aggregate material. In Step 3, an aqueous solution containing urea and a source of calcium ions, such as calcium chloride, is fed to the aggregate material. In Step 4, the urease enzyme broth solution, preferably containing the cells, is fed to the aggregate material. Steps 3 and 4 may be done simultaneously or at different times or in different order. In addition, the urea and the calcium ions may be in the same or different solutions. In Step 5, calcium carbonate crystals form between at least some of the gaps between the loose pieces of aggregate material. In Step 6, it is preferred that additional aqueous solution containing urea and calcium ions is fed to the aggregate material to reach the desired hardness of the brick. In Step 7, Steps 5 and 6 may be repeated until a desired hardness is reached. In Step 8, the formwork 24 is rotated, which in the embodiment of FIG. 2 is 180°. After rotation, Steps 1 through 7 are repeated. For combining the lamination method with the rotational method, in Step 2, the formwork 24 is not completely filled with aggregate but is only partially filled so as to form a layer. The solutions are applied to that layer of aggregate as set forth in Steps 3 through 7 and then the formwork may be rotated as set forth in Step 8. Once that layer has reached a degree of hardness, an additional layer of aggregate is fed to formwork 24 over the top of the hardened layer and Steps 3 through 8 are repeated. Additional layers can also be formed in a like manner.

Figure 4:
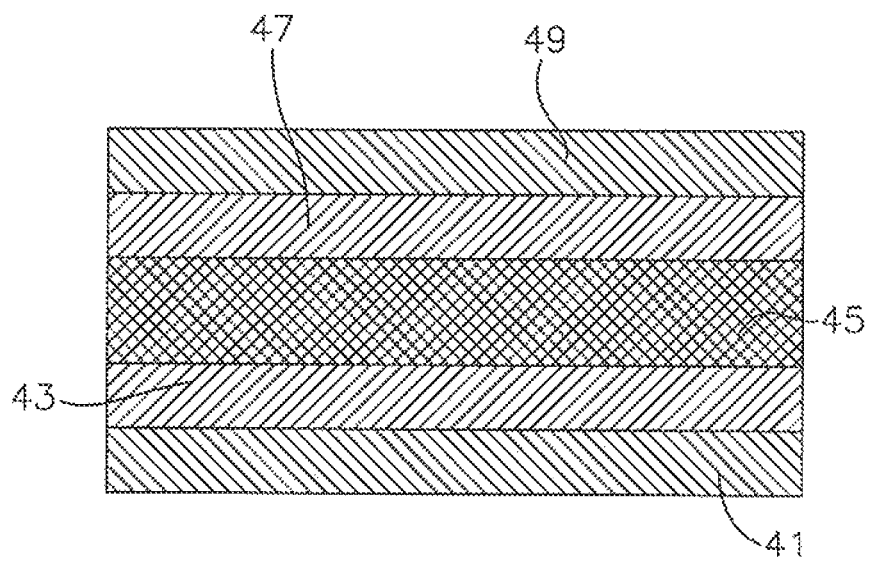
FIG. 4 is a side elevational view showing multiple layers of bonded aggregate formed using the embodiment of FIGS. 2 and 3.

FIG. 4 illustrates the striations or layers formed by the combination of the lamination and rotational methods referred to above. Layers 41, 43, 45, 47 and 49 are discrete layers. The sand within each layer is bonded and the sand at the boundaries of adjacent layers is also bonded forming a solid brick. The layering or lamination method allows for a programmed structure for the brick, for example, larger aggregate and particle distribution. It also allows for homogeneity of cementation. The calcium carbonate crystals, which form the bonds, are allowed to grow in between the layers so as to bond the layers together. The layering method of fabricating biomanufactured construction material allows for greater consistency in cementation and possibly over-all structural performance. The layering of the aggregate material allows for programmed structure and distribution of aggregate particle sizes, that is, larger aggregate particles may be used as structure.

Figure 6:
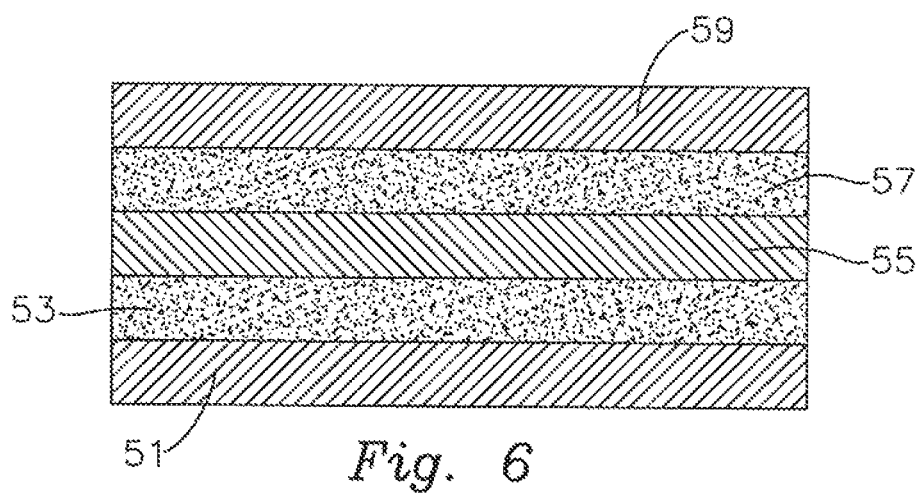
FIG. 6 is a side elevational view also showing multiple layers of bonded aggregate formed using the embodiment of FIGS. 5 and 6.

The preferred embodiment of carrying out the layering or lamination method is through the use of a computer numerical controlled (CNC) deposition machine, such as a 3-D printer, an embodiment of which is illustrated in FIG. 6, although other means may be employed, including manually layering by hand or mechanically layering through mass production.

Figure 5:
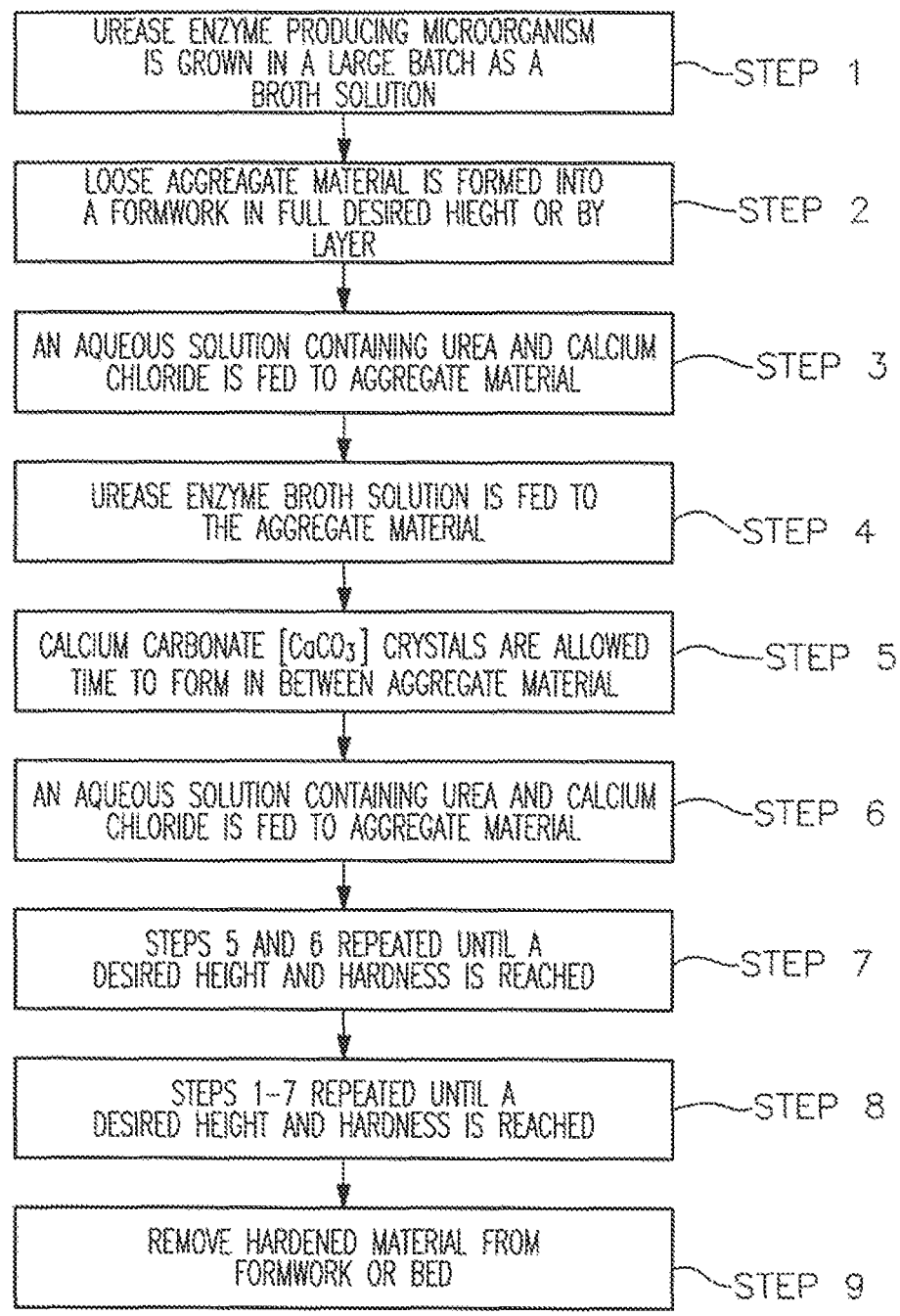
FIG. 5 is a flow chart showing steps for the production of construction material in accordance with another embodiment of the invention.

FIG. 5 illustrates an embodiment of the lamination or layering method of producing construction material. As illustrated in Step 1, urease producing cells, such as one of those listed above, is grown in a batch of broth solution with a growth media, such as urea, forming urease. A growth nutrient such as yeast extract or soy peptone is also added to the broth. As shown in Step 2, a layer of loose aggregate material is placed in a formwork or spread over a bed or substrate. As shown in Step 3, an aqueous solution containing urea and calcium ions, which may be obtained from calcium chloride, is fed to the aggregate material. The urease solution is fed to the aggregate material. Again, the solutions from Step 3 and Step 4 may be added to the aggregate simultaneously, at different times, or in a different order. In addition, the urea and the calcium ions may be in the same or different solutions. As shown in Step 5, calcium carbonate crystals form between the gaps in the pieces of aggregate material. As shown in Step 6, another aqueous solution containing urea and calcium chloride is fed to the aggregate material. As shown in Step 7, Steps 5 and 6 are repeated until a desired hardness is reached. As shown in Step 8, Steps 1 through 7 are repeated, thereby forming a number of layers, until a desired height and hardness are reached. As shown in Step 9, the hardened material, with the layers bonded together, is removed from the formwork, the bed or the substrate. Thus, solid layered material is formed from the loose aggregate.

FIG. 6 illustrates multiple layers which are bonded together to form the construction material which is made by the embodiment of FIG. 5. The aggregate within layers 51, 53, 55, 57 and 59 are bonded together and the adjacent layers at their boundaries are bonded together forming a solid brick.

FIG. 7 shows a computer numerical controlled (CNC) deposition machine which may be utilized to produce construction material using the layering or lamination method. Existing computer numerical controlled (CNC) platforms may be used and are commercially available from the MultiCam company (Series 5000 Model 508), although such platforms need to be modified as discussed below. Essentially, CNC deposition machine 44 is a MultiCam Series 5000 Model 508 which has been modified by adding the items shown in FIGS. 8 and 9, and spreader 54 and bed or substrate 46 thereto. The use of CNC technology is economically driven as it generates little waste, accommodates a variety of potential materials, provides a high degree of accuracy, and allows for large variations. Thus, the individual units of construction material are not bound by repeatable formwork or conventional forms. Rather, each unit of construction material can either be the same or different depending on the desired form and utilization. CNC deposition machine 44 is a three axes computer controlled printer for producing laminated or layered construction materials utilizing the lamination or layering method of the invention. A horizontal platform or substrate 46 is provided. The platform 46 may be specified in any dimension in the X and Y axes. The platform is supported by a hydraulic lift or other elevating mechanism for producing movement vertically, i.e., in the Z axis. Gantry 48 commands the Y axis and moves along rails 50 and 52 in the X axis by utilizing stepper motors. A dispensing nozzle unit 76 moves along rails in the Y axis by utilizing stepper motors. A microprocessor coordinates X-axis, Y-axis, and Z-axis movements to accurately locate the printer nozzle in 3-Dimensional space from user provided data, such as a digital model. Elongated container 54 holds the loose pieces of aggregate, such as sand, and serves as the aggregate spreader. Container 54 extends across substantially the width of substrate 46.

CNC deposition machine 44 includes solution containment clusters, namely, cluster 56 and another cluster 58. The solution containment clusters each include three containers, namely, container 60 which contains calcium chloride whereby calcium ions are in solution, container 62 which contains urea in solution, and container 64 which contains urease enzyme solution which was formed from combining the enzyme producing bacteria, which preferably is *Sporosarcina pasteurii*. Normally, container 64 also includes an amount of the bacteria.

Figure 8:
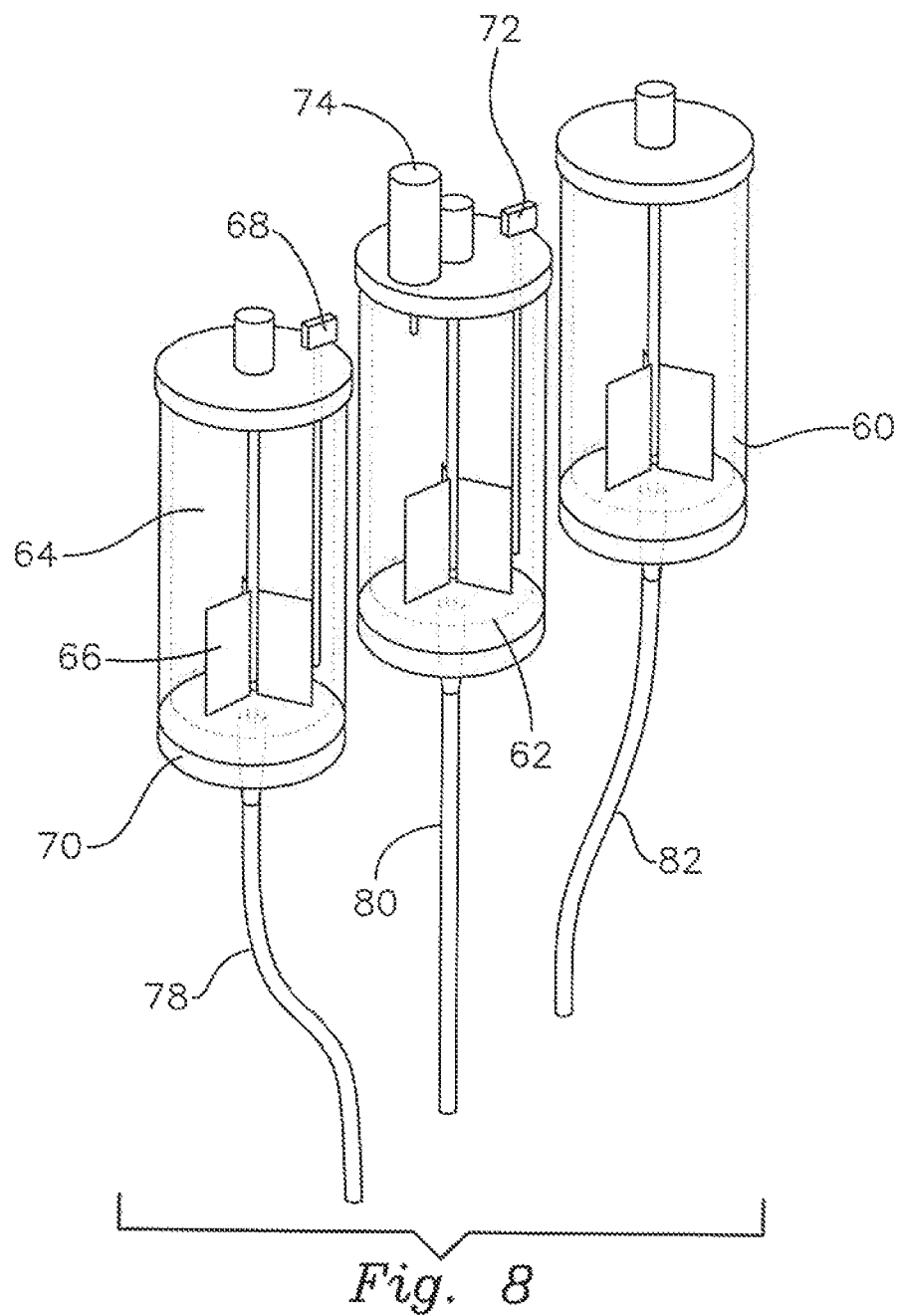
FIG. 8 is a pictorial view showing details of a portion of the computer numerical controlled deposition machine shown in FIG. 7.

FIG. 8 shows container cluster 56 in more detail. Each container 60, 62 and 64 includes a motor driven mixer 66. The motor driven mixer keeps the contained solution homogeneous. Urease enzyme solution container 64 also includes a temperature sensor 68 and warming element 70 to maintain optimum microorganism growth conditions. The urea solution container 62 includes a pH sensor 72 and a buffer solution dispenser 74 for maintaining an optimal concentration of hydrogen ions.

Figure 9:
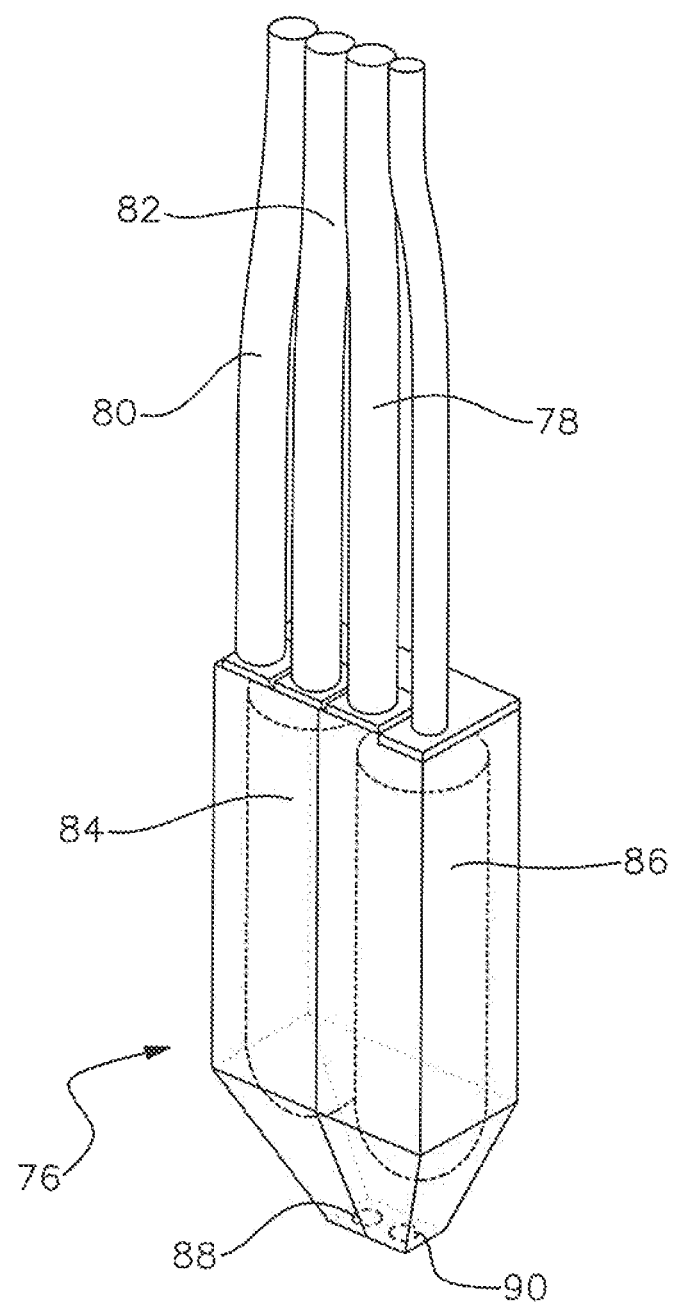
FIG. 9 is a perspective view showing details of an additional portion of the computer numerical controlled deposition machine shown in FIG. 7.

FIG. 9 illustrates a dispensing nozzle 76 for each solution containment cluster, such as cluster 56. Hoses 78, 80 and 82 connect respective containers 60, 62 and 64 to nozzle 76. Urea from container 62 is mixed with calcium ions from calcium chloride from container 60 in reservoir 84 which is received within dispensing nozzle 76. Urease enzyme and preferably an amount of bacteria are received from container 64 to reservoir 86. Opening 88 and dispensing nozzle 76 are connected to urea and calcium ions from calcium chloride reservoir 84 for applying urea and calcium ions to the layer of aggregate which has been deposited on substrate 46. Opening 90 connects to urease enzyme reservoir 86 for depositing urease enzyme solution onto the aggregate material which has been deposited on substrate 46. Computer control valves, such as solenoids, regulate the mixing of urea and calcium ions as the solutions are released from their respective reservoirs. Computer control valves also regulate the release of the solutions from the reservoirs through their respective openings 88 and 90.

The CNC deposition machine 44 operates as follows. Gantry 48 moves horizontally in one direction across the entire substrate 46 along the X axis depositing a single layer of aggregate material from aggregate container 54. Gantry 48 then returns to its initial position. Gantry 48 then moves one position along the X axis. The dispensing nozzles 76 move horizontally in another direction along the Y axis depositing an urease enzyme solution and a solution of urea and calcium ions onto individual units of sand 92, which in this embodiment are rectangular, which is specified by the user's input. The dispensing nozzles then return to their initial position. The steps of depositing the solution are repeated until gantry 48 reaches the end of the X axis whereby one layer of the construction material, such as brick, is formed. Gantry 48 then returns to its initial position. As an option, the solutions may again be deposited on the same layer of sand to achieve stronger cementation. The elevated substrate 46 then moves downwardly one position in the Z axis. The steps above are repeated until the desired material height is reached. Multiple cemented layers bonded together forming individual units are thus formed. The uncemented aggregate material, that is the aggregate material which is between individual units 92, is removed from the substrate. The layered cemented units are then removed from the substrate.

Alternatively, the solution dispenser nozzles and/or containment clusters may be utilized in conjunction with other computer numerical controlled platforms, such as six and seven axes robotic arms, for the precision location of solutions.

The following examples illustrate embodiments of the invention, but should not be viewed as limiting the scope of the invention.

EXAMPLES

Example 1—Cementation Tests

General cementation tests were performed in 60 ml cylinders with aggregate to test various method sequences and aggregate types. Consecutively, multiple formwork tests were performed in the scale of a 1:1 construction unit measuring 3.5 inches×2.25 inches×8 inches [88.90 mm×57.15 mm×203.20 mm] and a scaled version of a construction unit measuring 3 cm×1.5 cm×5 cm.

*Sporascarina pasteurii* [DSMZ 33] was inoculated in a "bacteria solution" DSMZ 220 media modified with urea, transferred to plate for colony growth and incubated at 25° C. for later use. General "cementation solutions" were prepared using 0.28% Tryptic Soy Broth made by Scharlau 117-333 mM urea [$(NH_2)_2CO$], 130-187 mM ammonium chloride [$NH_4Cl$], 25 mM sodium hydrogen carbonate [$NaHCO_3$], 55 mM calcium chloride [$CaCl_2$], and 1 L of distilled water. Medias were filter sterilized to insure against contamination. A concentration of 55 mM calcium chloride dihydrate was prepared as an aqueous solution for the calcium ions used in the cementation process.

Three 60 ml syringes were each filled with [A] 5 g Poraver™ 2 mm-1 mm [porous glass beads], [B] 30 g sieved 600-212 microns of locally sourced sand found in Sharjah, United Arab Emirates [UAE] and [C] 30 g 600-75 microns of the same sand. The samples were then vibrated for granular settlement and plungers were applied to confine the sand in the form. This process also reduces the air between grains of sand, air entrained in the system could cause a fracture point in the final hardened material due to the resulting formation of a bubble void.

A flexible 4 mm ID silicon hose was inserted into the top of the syringe plunger as an influent line, and another 4 mm ID tube was inserted into the syringe bottom as an effluent line.

The tests were first fed Solution 1 "Bacteria Solution" at a gravity flow rate as approximately three pore volumes [PV] of media. After allowing the bacteria to "set" for six hours, the tests were then fed Solution 2 "Cementation Solution" as three PV of media at a gravity flow rate after which the solution was allowed to "set" for 4-12 hrs. This sequence was alternated for the UAE sand samples. This process continued until hardness was reached. The tests were flushed with tap water and allowed to air dry.

All three samples exhibited cementation. The samples were weighed to determine gained mineral material. After weighing, the samples were prepared for Scanning Electron Microscopy [SEM] to visually verify crystal formations and bonded grains of aggregate. FIG. 10 illustrates sample C.

| Sample | Starting Weight | Final Weight | Gained Weight |
|---|---|---|---|
| A Poraver™ | 5 g | 10.21 g | 5.21 g |
| B Sharjah 600-212 microns | 30 g | 39.94 g | 9.94 g |
| C Sharjah 600-75 microns | 30 g | 37.07 g | 7.07 g |

Bacterial colonies on plates were stored in a 25° C. incubator. The bacteria solution batches were grown aerobically with an incubated shaker set at 37° C., 250-300 RPM for 20-24 hours. A Tinius Olsen H50TK compression-testing machine was used to determine the compressive strength value of the final hardened material. As an example, the sand sample [C] reached 16.58 MPa as a compressive strength. The overall hardness and strength can be increased with additional cementation solution treatments.

Example 2—Rotation Method

To create a greater strength and more unified cementation throughout the aggregate, a rotation method was developed for a full-scale "brick" form. A batch of bacteria solution was prepared using the same method as example 1. Simultaneously, a batch of cementation solution set to 7.25 pH was prepared using the same media as example 1. 1700 g of non-sterile aggregate in the form of indigenous sand found in Sharjah, UAE was sieved to 2 mm-212 microns and placed into the formwork, after a polyester fiber filter was applied. The formwork was then vibrated to reduce air between the aggregate, another polyester fiber filter was placed on top of the dry aggregate, and the formwork top with influent holes was lastly positioned. The formwork is the same as in FIG. 2. Full scale construction unit formwork in the form of a building unit [3.5 inches×2.25 inches×8 inches] was fabricated of 5 mm cast acrylic using Universal Systems 50 Watt laser cutter for precise and reusable breakaway formwork.

15 ml of 55 mM $CaCl_2$ was added to 750 ml of the prepared cementation solution. The solution was then fed to the formwork via gravity feed through the influent holes. As soon as the effluent began to leave the formwork, the effluent valves were then shut off to "trap" the solution in the formwork between voids in the aggregate. The solution was allowed to set in the formwork for approximately 15 minutes.

750 ml of bacteria solution with live cells was then fed to the formwork via gravity feed through the influent holes. Effluent was allowed to leave the formwork until the cementation solution reached the end of the influent holes after which the effluent valves were then shut off to "trap" the solution in the formwork between voids in the aggregate. The solution was allowed to set in the formwork for 4-12 hours.

Another batch of cementation solution with urea and calcium chloride was prepared and fed to the formwork via gravity feed through the influent holes. As the effluent began to leave the formwork, the effluent valves were then shut off to "trap" the solution in the formwork between voids in the aggregate for 4-12 hours. This process was repeated again 5-10 times.

The formwork was then rotated 180 degrees along one axis with the bottom of the formwork becoming the top and the top becoming the bottom.

Another batch of cementation solution with urea and calcium chloride was prepared and fed to the formwork via gravity feed through the influent holes. As soon as the effluent began to leave the formwork, the effluent valves were then shut off to "trap" the solution in the formwork between voids in the aggregate for 4-12 hours. This process was again repeated 5-10 times.

The formwork was then rotated again 180 degrees along one axis with the bottom of the mold now being on top. Rotation and administration of cementation solution continued until a desired hardness or strength was reached. The hardened construction material was removed from the formwork, washed with tap water and allowed to air dry.

After the material was dried and weighed, the resulting material was homogenously cemented on all sides. The cemented material was mechanically split along the center and cementation was verified along the cross section of the interior.

Example 3—Slurry Method

The slurry method used the same media and methods as the above example, with the exception that the two solutions and aggregate were combined forming an aqueous slurry of aggregate, bacteria solution, urea, and calcium chloride. The slurry was then placed in the same design of formwork as described in example 2 with the exception of a change in dimension to 3 cm×1.5 cm×5 cm. Effluent valves were shut off to "trap" the solution in the formwork between voids in the aggregate and allowed to set for 3-8 hours.

Another batch of cementation solution with urea and calcium chloride was prepared and fed to the formwork via gravity feed through the influent holes. As soon as the effluent began to leave the formwork, the effluent valves were then shut off to "trap" the solution in the formwork between voids in the aggregate for 4-12 hours. This process was repeated 5-10 times.

The formwork was then rotated along one axis with the bottom of the formwork now being on top [Side A]. Another batch of cementation solution with urea and calcium chloride was prepared and fed to the formwork via gravity feed through the influent holes. As soon as the effluent began to leave the formwork, the effluent valves were then shut off to "trap" the solution in the formwork between voids in the aggregate for 4-12 hours. This was repeated 5-10 times.

The formwork was then rotated 180 degrees along one axis with the bottom of the formwork becoming the top and the top becoming the bottom. Rotation and administration of cementation solution continued until a desired hardness and strength was reached.

The hardened material in the form of a "brick" was removed from the formwork, washed with tap water and allowed to air dry. All sides were cemented.

Example 4—Lamination Method [Analog]

The lamination method used the same media and methods as example 2 with the exception that the aggregate material was placed into the formwork as distinct layers. This enables the final material to have different degrees of aggregate particle size distribution, and a more homogeneous cementation within the overall unit.

A 5 mm layer of non-sterile aggregate in the form of indigenous sand found in Sharjah, UAE was sieved to 600 microns-212 microns and placed into the formwork. The formwork was lightly vibrated to reduce air between aggregates.

2 ml of 55 mM $CaCl_2$ was added to 50 ml of the prepared cementation solution. The solution was then fed to the formwork via gravity feed through the influent holes. The solution was allowed to set in the formwork for approximately 15 minutes.

50 ml of bacteria solution with live cells was then fed to the formwork via gravity feed through the influent holes. The solution was allowed to set in the formwork for 4-12 hours. Another batch of cementation solution with urea and calcium chloride was prepared and fed to the formwork via gravity feed through the influent holes. This was repeated 5-10 times.

Another layer of 5 mm non-sterile aggregate was placed into the formwork, on top of Layer 1. The process as described for layer 1 was repeated until the full height and desired hardness and strength of the final unit was reached, with a total of 3 layers.

The hardened material was removed from the bed, washed with tap water and allowed to dry.

Example 5—Lamination+Rotation Method [3 cm×1.5 cm×5 cm]

The lamination+rotation method used the same media and methods as described examples 2 and 4, with the exception of each layer being rotated and treated on both sides prior to the addition of each successive layer.

Example 6—Lamination Method [Digital Rapidly Manufactured]

A modified "Fab at Home" CNC 3D printer [open source 3D printer platform] was used to precisely deposit the solutions over a bed of sand material for rapid manufactured tests.

A batch of Solution 1 "Bacteria Solution' was prepared using the same method as example 1. Simultaneously, a batch of Solution 2 "Cementation Solution" set to 7.25 pH was prepared using the same media as example 1.

A 5 mm layer of non-sterile aggregate in the form of indigenous sand found in Sharjah, UAE was sieved to 600 microns-212 microns and placed onto the substrate bed of the 3D Printer.

1 ml of 55 mM of $CaCl_2$ was added to 25 ml cementation solution and mixed with 25 ml of the bacteria solution. This was then placed in the deposition syringe of the 3D printer. The syringe motor was controlled via a computer model and the 51 ml of cells and cementation solution was precisely deposited as discrete droplets on top of the sand substrate as multiple passes. The deposition syringe was reloaded and cleaned as necessary.

The solutions were allowed to set in the sand for 3 hours, after which a new preparation of cementation solution was prepared and set to 7.25 pH. This new solution was placed into the syringe and deposited over the sand substrate. The solution was allowed to set in the sand for 3 hours, after which a new preparation of cementation solution was prepared and set to 7.25 pH. This process continued for a total of 5 treatments.

A new 5 mm layer of non-sterile aggregate [same composition as layer 1] was sieved to 600-425 microns and evenly placed onto the substrate over layer 1. The process as described for layer 1 was then repeated for layer 2 and again for layer 3.

A new preparation of cementation solution was prepared and set to 7.25 pH. This solution was placed in the syringe of the 3D printer and deposited over the top of the hardened sand over multiple passes. This step served as a "finishing" pass of cementation media. The hardened material was removed from the bed, washed with tap water and allowed to dry.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. The term comprising, where ever used, is intended to include the terms consisting and consisting essentially of. Furthermore, the terms comprising, including, and containing are not intended to be limiting. It is intended that the specification and examples be considered exemplary only with the true scope and spirit of the invention indicated by the following claims.

The invention claimed is:

1. A solid structure comprising a plurality of aggregate particles bound together with calcite bonds, wherein the calcite bonds are distributed equally around aggregate particles.

2. The solid structure of claim 1, wherein the plurality of aggregate particles comprises particles of sand, crushed stone, basalt, glass, gravel, clay, recycled brick, recycled cement, or mixtures thereof.

3. The solid structure of claim 1, wherein the solid structure further comprises performance enhancing materials.

4. The solid structure of claim 3, wherein the performance enhancing materials comprise fibers that provide strength to the solid structure.

5. The solid structure of claim 3, wherein the performance enhancing materials comprise pollution absorbing materials.

6. The solid structure of claim 5, wherein the pollution absorbing materials comprise titanium dioxide.

7. The solid structure of claim 3, wherein the performance enhancing materials comprise insulation materials.

8. The solid structure of claim 3, wherein the performance enhancing materials comprise materials that enhance light transmission.

9. The solid structure of claim 8, wherein the materials that enhance light transmission comprise glass.

10. The solid structure of claim 1, which have a predetermined hardness.

11. The solid structure of claim 1, which has a compression strength greater than a clay brick.

12. A solid structure comprising a homogenous plurality of aggregate particles bound together with calcite bonds, wherein the calcite bonds are distributed equally around aggregate particles and manufactured by combining aggregate particles, calcium, urea and urease in an aqueous mixture forming calcite bonds.

13. The solid structure of claim 12, wherein the aggregate particles comprise sand, stone, gravel, basalt, glass, clay, asphalt, or mixtures thereof.

14. The solid structure of claim 12, wherein the calcium comprises one or more of calcium chloride, calcium acetate, calcium phosphate, calcium sulfate, or mixtures thereof.

15. The solid structure of claim 12, wherein the urease is produced from microorganisms.

16. The solid structure of claim 15, wherein the microorganisms comprise one or more of cells and/or spores of *Sporosarcina ureae, Proteus vulgaris, Bacillus sphaericus, Myxococcus xanthus, Proteus mirabilis* and *Helicobacter pylori*, or combinations thereof.

17. The solid structure of claim 12, wherein the solid structure further contains performance enhancing materials that comprise materials that enhance strength, enhance absorb pollution, enhance light transmission, and/or enhance insulation of the solid structure.

18. The solid structure of claim 12, wherein the solid structure comprises a predetermined shape.

19. The solid structure of claim 12, wherein the predetermined shape is a brick, a block, a tile, a column, and/or a panel.

* * * * *